United States Patent [19]
Thompson et al.

[11] Patent Number: 5,502,060
[45] Date of Patent: Mar. 26, 1996

[54] HIV PROTEASE INHIBITORS

[75] Inventors: Wayne J. Thompson; Arun K. Ghosh, both of Lansdale; Joel R. Huff, Gwynedd Valley; Hee Y. Lee, Hatfield, all of Pa.

[73] Assignee: Merck & Co., Inc., Rahway, N.J.

[21] Appl. No.: 328,936

[22] Filed: Oct. 25, 1994

Related U.S. Application Data

[63] Continuation of Ser. No. 144,094, Oct. 27, 1993, abandoned, which is a continuation of Ser. No. 929,991, Aug. 21, 1992, abandoned, which is a continuation-in-part of Ser. No. 781,470, Oct. 23, 1991, abandoned.

[51] Int. Cl.$^6$ .................. C07D 217/02; A61K 31/47
[52] U.S. Cl. .................................... 514/307; 546/147
[58] Field of Search .................. 546/147; 514/307

[56] References Cited

FOREIGN PATENT DOCUMENTS

| | | |
|---|---|---|
| 0346847 | 12/1989 | European Pat. Off. . |
| 0389898 | 3/1990 | European Pat. Off. . |
| 0434365A2 | 6/1991 | European Pat. Off. . |
| 0432695 | 6/1991 | European Pat. Off. . |
| 0432694 | 6/1991 | European Pat. Off. . |

OTHER PUBLICATIONS

Roberts, N.A., et al. "Rational Design of Peptide–Based HIV Proteinase Inhibitors," Science, vol. 248, pp. 358–361 (1990).
Kohl, N. E. et al., "Active HIV protease is required for viral infectivity," Proc. Natl. Acad. Sci. 85, 4686 (1988).
Ratner, L. et al., "Complete nucleotide sequences of . . . HTLV–III," Nature 313, 277 (1985).
Toh, H. et al., "Close structural resemblance . . . ," EMBO J. 4, 1267 (1985).
Power, M. D. et al., "Nucleotide Sequence of SRV–1 . . . ," Science 231, 1567 (1986).
Pearl, L. H. et al., "A Structural Model for the retroviral proteases," Nature 329, 351 (1987).
Skiles, J. W. et al., J. Med. Chem., 29, 784 (1986).
Hein, G. E., et al., "Steric Course and Specificity of Alpha––Chymotrypsin Catalyzed Reactions," J. Am. Chem. Soc. 84, 4489 (1962).
Hayasnik, K. et al., Chem. Pharm. Bull. 31, 312 (1983).
Gao, Y. et al., "Catalytic Asymmetric Epoxidation . . . ," J. Am. Chem. Soc. 109, 5765 (1987).
Caron, M. et al., "Regioselective Azide Opening of 2,3–Epoxy Alcohols . . . ," J. Org. Chem. 53, 5185 (1988).
Ghosh, A. K. et al., Tetrahedron Lett. 32, 4241 (1991).
Jalali–Naini, M. et al., Tetrahedron Lett., 497 (1986).

Primary Examiner—Bernard Dentz
Assistant Examiner—Zinna N. Davis
Attorney, Agent, or Firm—Roy D. Meredith; Charles M. Caruso

[57] ABSTRACT

Oligopeptide analogs are described. These compounds are useful in the inhibition of HIV protease, the prevention or treatment of infection by HIV and the treatment of AIDS, either as compounds, pharmaceutically acceptable salts, pharmaceutical composition ingredients, whether or not in combination with other antivitals, immunomodulators, antibiotics or vaccines. Methods of treating AIDS and methods of preventing or treating infection by HIV are also described.

13 Claims, No Drawings

HIV PROTEASE INHIBITORS

This application is a continuation of Ser. No. 08/144,094, filed Oct. 27, 1993, now abandoned, which is a continuation of Ser. No. 07/929,991, filed Aug. 21, 1992, now abandoned, which is a continuation-in-part of Ser. No. 07/781,470, filed Oct. 23, 1991, now abandoned.

The present invention is concerned with compounds which inhibit the protease encoded by human immunodeficiency virus (HIV). The compounds, or pharmaceutically acceptable salts thereof, are of value in the prevention of infection by HIV, the treatment of infection by HIV and the treatment of the resulting acquired immune deficiency syndrome (AIDS).

The present invention also relates to pharmaceutical compositions containing the compounds and to a method of use of the present compounds and other agents for the treatment of AIDS & viral infection by HIV.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a vitally encoded protease to generate mature vital proteins required for virus assembly and function. Inhibition of this processing prevents the production of normally infectious virus. For example, Kohl, N. E., et. al., Proc. Natl. Acad. Sci. USA, 85, 4686 (1988), demonstrated that genetic inactivation of the HIV encoded protease resulted in the production of immature, non-infectious virus particles. These results suggest that inhibition of the HIV protease represents a viable method for the treatment of AIDS and the prevention or treatment of infection by HIV.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, an endonuclease and an HIV protease [Toh, H. et al., EMBO J. 4, 1267 (1985); Power, M. D. et al., Science, 231, 1567 (1986); Pearl, L. H. et al., Nature 329,351 (1987)]. Applicants demonstrate that the compounds of this invention are inhibitors of HIV protease.

Related art includes Hoffman-LaRoche EPO applications. EPO 389898, EPO 346847, and EPO 432695 each disclose HIV protease inhibitors but the compounds are very different because they have an amino acid (or analog thereof) attached to the amino-terminal end of the transition state analog. EPO 432694 discloses synthetic intermediates which are different from the compounds of the present invention.

The particular advantages of the compounds of the present invention are increased oral bioavailability and lower serum protein binding.

BRIEF DESCRIPTION OF THE INVENTION

Compounds of formula I, as herein defined, are disclosed. These compounds are useful in the inhibition of HIV protease, the prevention of infection by HIV, the treatment of infection by HIV and in the treatment of AIDS, either as compounds, pharmaceutically acceptable salts, hydrates or esters, pharmaceutical composition ingredients, whether or not in combination with other antivirals, immunomodulators, antibiotics or vaccines. Methods of treating AIDS, methods of preventing infection by HIV, and methods of treating infection by HIV are also disclosed.

| ABBREVIATIONS | |
|---|---|
| | Activating Agent |
| HBT (HOBT or HOBt) | 1-hydroxybenzotriazole hydrate |
| | Condensing Agent |
| EDC | 1-ethyl-3-(3-dimethylamino-propyl)carbodiimide |

DETAILED DESCRIPTION OF THE INVENTION AND PREFERRED EMBODIMENTS

This invention is concerned with the compounds of Formula I, combinations thereof, or pharmaceutically acceptable salts thereof, in the inhibition of HIV protease, the prevention of infection by HIV, the treatment of infection by HIV and in the treatment of the resulting acquired immune deficiency syndrome (AIDS). Compounds of formula I are defined as follows:

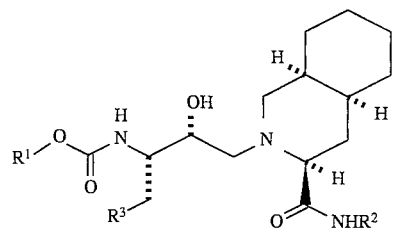

wherein:

$R^1$ is a) 5- to 7- membered carbocylic ring which is either saturated, partially saturated or unsaturated, the carbocylic ring being unsubstituted or substituted with one or more of $C_{1-4}$ alkyl, $C_{2-4}$ alkenyl, $C_{1-3}$ alkoxy, halo-$C_{1-3}$ alkyl, aryl-$C_{1-3}$ alkyl, or $C_{3-5}$ cycloalkyl; or b) 5- to 7-membered heterocyle having one heteroatom selected from O or S, any of which heterocycle is unsubstituted or substituted with one or more of $C_{1-4}$ alkyl, $C_{2-4}$ alkenyl, oxo, $C_{3-5}$ cycloalkyl, or $C_{1-3}$ alkoxy;

$R^2$ is a) $C_{1-5}$ alkyl, unsubstituted or substituted with one or more of —OH or $C_{1-3}$ alkoxy; or b) 5- to 7-membered carbocyclic ring which is either saturated, partially saturated or unsaturated, the carbocyclic ring being unsubstituted or substituted with one or more of $C_{1-4}$ alkyl, $C_{2-4}$ alkenyl, $C_{1-3}$ alkoxy, or hydroxy;

$R^3$ is a) Phenyl unsubstituted or substituted with one or more of —OH or $C_{1-3}$ alkoxy; or b) $C_{5-7}$ cycloalkyl unsubstituted or substituted with one or more of —OH or $C_{1-3}$ alkoxy, or pharmaceutically acceptable salt or hydrate thereof.

The compounds of the present invention may have asymmetric centers and occur as racemates, racemic mixtures and as individual diastereomers or enantiomers, with all isomeric forms being included in the present invention.

When any variable (e.g., heterocycle, $R^1$ or $R^2$, etc.) occurs more than one time in any constituent or in formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents an alkyl group of indicated number of carbon atoms attached through an oxygen bridge. "Alkenyl" is intended to include hydrocarbon claims of either a straight or branched configuration and one or more unsaturated carbon-carbon bonds which may occur in any stable point along the chain, such as ethenyl, propenyl, butenyl, pentenyl, and the like. "Halo", as used herein, means fluoro, chloro, bromo or iodo.

As used herein, with exceptions as noted, "aryl" is intended to mean phenyl (Ph) or naphthyl. "Carbocyclic" is intended to mean any stable 5- to 7-membered carbon ring or 7- to 10-membered bicyclic carbon ring, any of which may be saturated or partially unsaturated.

The term heterocycle or heterocyclic, as used herein except where noted, represents a stable 5- to 7-membered monocyclic heterocyclic ring which is either saturated or unsaturated, and which consists of carbon atoms and from one to three heteroatoms selected from the group consisting of O and S, and wherein the sulfur heteroatoms may optionally be oxidized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include benzopyranyl, benzothiopyranyl, tetrahydrofuryl, tetrahydropyranyl, and tetrahydrothienyl.

The pharmaceutically-acceptable salts of the compounds of Formula I (in the form of water- or oil-soluble or dispersible products) include the conventional non-toxic salts or the quaternary ammonium salts of these compounds, which are formed, e.g., from inorganic or organic acids. Examples of such acid addition salts include acetate, adipate, alginate, aspartate, benzoate, bisulfate, citrate, digluconate, dodecylsulfate, fumarate, glycerophosphate, bemisulfate, hydrochloride, 2-hydroxyethanesulfonate, lactate, maleate, methanesulfonate, succinate and tartrate.

In a preferred embodiment of this invention, $R^1$ is a 5- to 7-membered heterocycle having one heteroatom selected from O or S, any of which heterocycle is unsubstituted or substituted with one or more of $C_{1-4}$ alkyl, $C_{2-4}$ alkenyl, oxo or $C_{1-3}$ alkoxy;

$R^2$ is $C_{1-5}$ alkyl, unsubstituted or substituted with one or more of —OH;

$R^3$ is phenyl unsubstituted or substituted with —OH or $C_{1-3}$ alkoxy.

A third embodiment is further limited to compounds wherein:

$R^1$ is 1,1-dioxo-tetrahydrothienyl or tetrahydrofuranyl, unsubstituted or substituted with $C_{1-4}$ alkyl, $C_{2-4}$ alkenyl or $C_{1-3}$ alkoxy;

$R^2$ is t-butyl or 2-methylpropyl;

$R^3$ is phenyl.

A fourth embodiment is further limited to compound wherein:

$R^1$ is tetrahydrofuran-3-yl or 1,1-dioxo-tetrahydrothien-3-yl, unsubstituted or substituted with methyl, ethyl, n-propyl, i-propyl, methoxy, ethoxy, or propenyl.

In a fifth preferred embodiment, $R^1$ is a 5- to 7-membered heterocycle having one S heteratom, said heterocycle unsubstituted or substituted with one or more of $C_{1-4}$ alkyl, oxo or $C_{3-5}$ cycloalkyl;

$R^2$ is $C_{1-5}$ alkyl;

$R^3$ is phenyl.

A sixth embodiment is further limited to:

$R^1$ is 1,1-dioxotetrahydrothien-3-yl, unsubstituted or substituted with $C_{1-4}$ alkyl, or $C_{3-5}$ cycloalkyl;

$R^2$ is $C_{1-5}$ alkyl;

$R^3$ is phenyl.

Most preferred compounds of this invention include the following:

A:

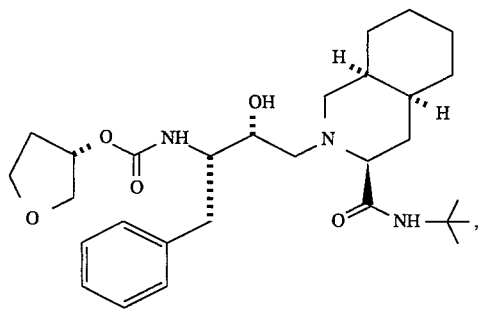

cis-N-tert-butyl-decahydro-2[2(R)-hydroxy-4-phenyl- 3(S)-[3(S)-tetrahydrofuranyloxycarbonylamino]-butyl]-( 4aS, 8aS)-isoquinoline-3(S)-carboxamide hydrate; or

B:

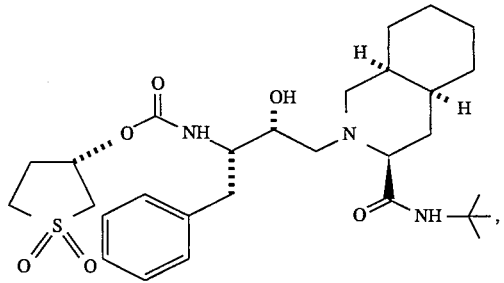

Cis-N-tert-butyl-decahydro-2[2(R)-hydroxy-4-phenyl-3(S)-[3(S)-1,1-dioxotetrahydrothien-3-yloxycarbonylamino ]-butyl]-(4aS, 8aS )-isoquinoline-3(S)-carboxamide hydrate;

C:

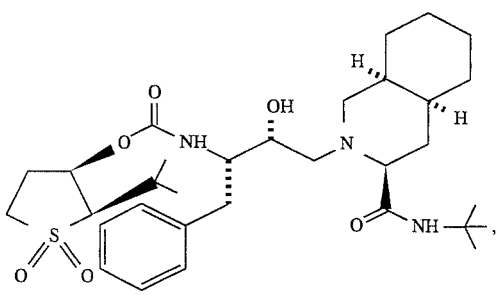

N-tert-butyl-decahydro-2[2(R)-hydroxy-4-phenyl-3(S)-[1,1-dioxo-2(R)-methylethyl-3(R)-tetrahydrothienyloxycarbonylamino ]butyl]-(4aS, 8aS)-isoquinoline-3(S)carboxamide, or pharmaceutically acceptable salt thereof.

The compounds of the present invention are prepared in accordance with Schemes I–IV.

SCHEME I

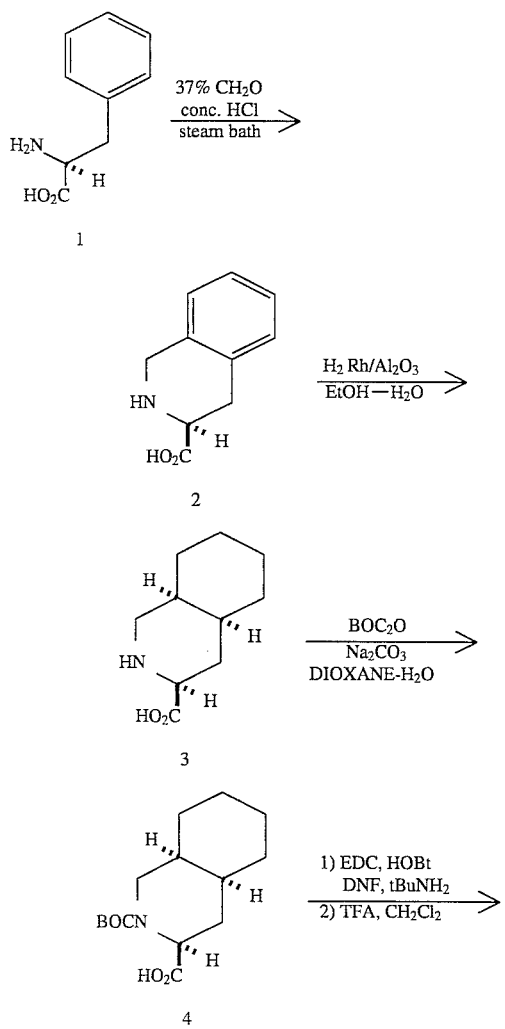

-continued
SCHEME I

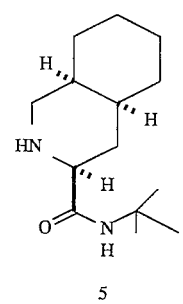

The decahydro-isoquinoline intermediate 5 is synthesized by a first reaction of L-phenylalanine with formaldehyde and concentrated HCl to produce 2, as also described in Skiles, J. W. et al., J. Med. Chem. 29,784 (1986) Hein, G. E., et al., J. Am. Chem. Soc. 48., 4487 (1962) and Hayasnik, K. et al., Chem. Pharm. Bull. 31, 312 (1983). Subsequent hydrogenation with catalysts such as Pt or Rh yields 3, which is then derivatized with an NH-protecting group such as Boc to give 4. Coupling with tBuNH$_2$ followed by deprotection affords 5. Example 1 illustrates but does not limit Scheme I.

SCHEME II

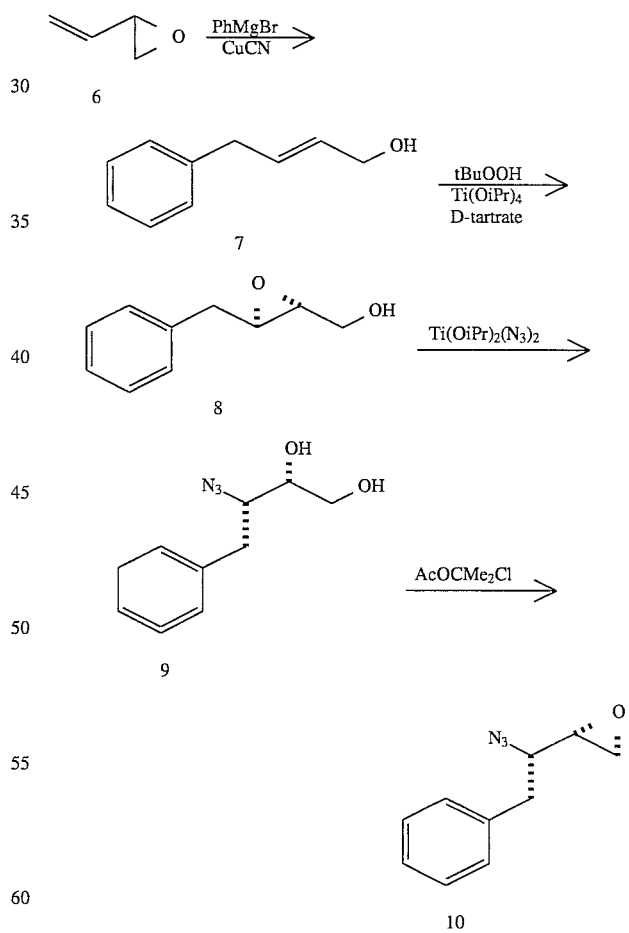

Catalytic asymmetric or Sharpless epoxidation to produce 8 is performed by the methods of Gao, Y. et al., J. Am. Chem. Soc. 109, 5765 (1987), Regioselective azide opening of the 2,3-epoxy alcohol 8 to give 9 is facilitated by titanium according to Caron, M. et al., J. Org. Chem. 53, 5185 (1988). Example 2 illustrates but does not limit Scheme II.

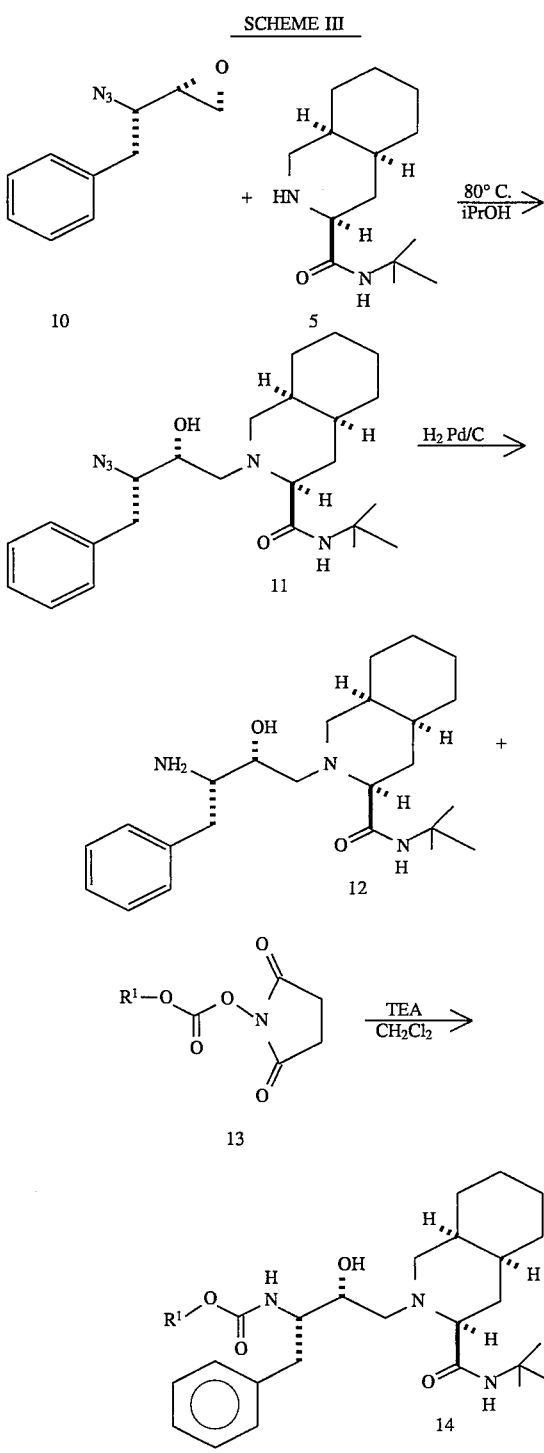

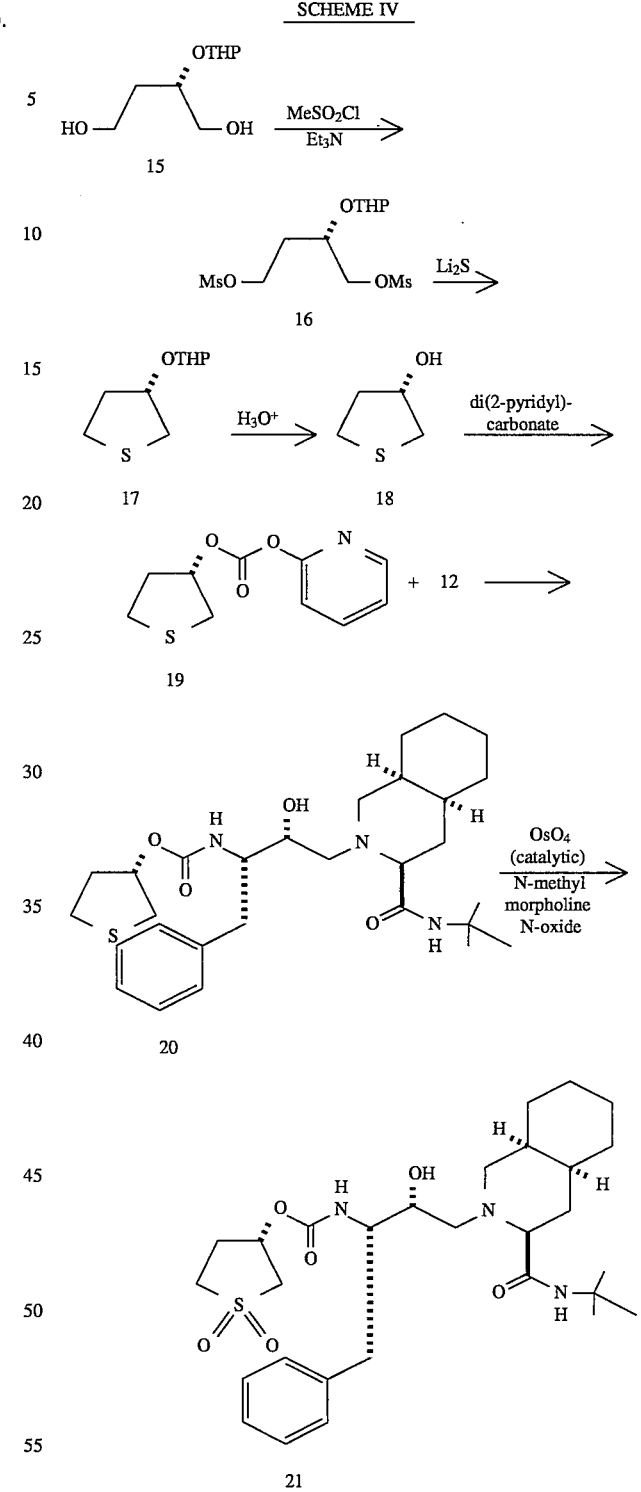

Condensation of the azide epoxide 10 with the decahydroisoquinoline intermediate 5 is performed by, for example, heating a mixture in refluxing isopropanol, to give the azido-alcohol 11 in good yield. Reduction over palladium on carbon yields the amine 12, which is then reacted with the appropriate N-substituted succinimide 13 in the presence of e.g. TEA to give compounds of Formula I or 14. Examples 3–6 illustrate but do not limit Scheme III.

Alternatively, for the synthesis of cyclic sulfone compounds such as compound 21, the di-(2-pyridyl) carbonate method of urethane coupling according to A. K. Ghosh, T. T. Duong and S. P. McKee, Tetrahedron Letters, 32, 4251 (1991) may be employed (Scheme IV). The (S)-butane-1,2, 4-triol-2-tetrahydropyranyl ether 15 is prepared according to K. Mori, T. Takigawa and T. Matsuo, Tetrahedron, 35,933 (1979) and converted into the 3(S)-hydroxytetrahydrothiophene 18 as shown in Scheme IV. Selective oxidation of the coupled tetrahydrothiophene 20 into the sulfolane 21 was effected by catalytic osmium tetraoxide in the presence of N-methylmorpholine N-oxide. Examples 7–12 illustrate but do not limit Scheme IV.

Other substituents for $R^2$ and $R^3$ in Formula I are readily prepared by those skilled in the art, by substituting and/or protecting appropriate groups in the schemes outlined above.

The compounds of the present invention include but are not limited by the following Table:

TABLE

[Structure: R—C(=O)—NH—CH(CH₂Ph)—CH(OH)—CH₂—N(decahydroisoquinoline)—C(=O)—NH—C(CH₃)₃]

| R | mp |
|---|---|
| (3S)-tetrahydrothiophene-yl | 106–8° C. |
| (3S)-tetrahydrothiophene-1,1-dioxide-yl | 111–113° C. |
| (3R)-tetrahydrothiophene-yl | 93–95° C. |
| (3R)-tetrahydrothiophene-1,1-dioxide-yl | 99–101° C. |
| 3-methoxy-tetrahydrothiophene-1,1-dioxide (trans) | — |
| 3-methoxy-tetrahydrothiophene-1,1-dioxide (cis) | — |
| 4-methoxy-tetrahydropyran-3-yl | 84–85° C. |

TABLE-continued

[Same core structure]

| R | mp |
|---|---|
| benzyl-tetrahydropyranyl | 95–96° C. |
| methyl-dihydropyranyl | 85–86° C. |
| methyl-tetrahydropyranyl | 86–89° C. |
| dihydropyran-3-yl | 87–88° C. |
| dihydropyran-3-yl (isomer) | 89–90° C. |
| (3S)-tetrahydrofuran-yl | 80–82° C. |
| (3R)-tetrahydrofuran-yl | 65–68° C. |
| 3-methyl-tetrahydrofuran-yl (trans) | — |
| 3-methyl-tetrahydrofuran-yl (cis) | — |
| 3-methoxy-tetrahydrofuran-yl (mixture of diastereomers) | 72–79° C. |

TABLE-continued

[Structure: R-C(=O)-NH-CH(CH2Ph)-CH(OH)-CH2-N(decahydroisoquinoline-C(=O)NH-tBu)]

| R | mp |
|---|---|
| (2-methyl-tetrahydrofuran-3-yl)oxy | |
| (5-iodomethyl-tetrahydrofuran-3-yl)oxy | 82–84° C. |
| (5-methyl-tetrahydrofuran-3-yl)oxy | |
| (tetrahydropyran-3-yl)oxy | 95–96° C. |
| (tetrahydropyran-3-yl)oxy | 92–93° C. |
| (tetrahydrothiopyran-3-yl)oxy | 94–97° C. |
| (tetrahydrothiopyran-3-yl)oxy | 94–96° C. |
| (1,1-dioxo-tetrahydrothiopyran-3-yl)oxy | |
| (chroman-3-yl)oxy | 196–97° C. |
| (2-methyl-1,1-dioxo-tetrahydrothiophen-3-yl)oxy | |

TABLE-continued

[Same parent structure]

| R | mp |
|---|---|
| (4-methyl-1,1-dioxo-tetrahydrothiophen-3-yl)oxy | |
| (4-methyl-1,1-dioxo-tetrahydrothiophen-3-yl)oxy | |
| (5-methyl-1,1-dioxo-tetrahydrothiophen-3-yl)oxy | |
| (5-methyl-1,1-dioxo-tetrahydrothiophen-3-yl)oxy | |
| (1,4-dioxaspiro bicyclic) | 109–112° C. |
| (2-methyl-1,1-dioxo-tetrahydrothiophen-3-yl)oxy | |
| (2-isopropyl-1,1-dioxo-tetrahydrothiophen-3-yl)oxy | 115–7° C. |

TABLE-continued

[Structure: R-C(=O)-NH-CH(CH2-Ph)-CH(OH)-CH2-N(decahydroisoquinoline)-C(=O)-NH-C(CH3)3]

| R | mp |
|---|---|
| [tetrahydrothiophene-1,1-dioxide with isopropyl substituent] | 110–2° C. |
| [tetrahydrothiophene-1,1-dioxide with sec-butyl substituent] | 189–91° C. |
| [tetrahydrothiophene-1,1-dioxide with sec-butyl substituent] | 182–4° C. |
| [tetrahydrothiophene-1,1-dioxide with sec-butyl substituent] | 105–13° C. |
| [tetrahydrothiophene-1,1-dioxide with sec-butyl substituent] | 112–8° C. |
| [tetrahydrothiophene-1,1-dioxide with cyclopentyl substituent] | amorphous |
| [tetrahydrothiophene-1,1-dioxide with cyclopentyl substituent] | amorphous |

The compounds of the present invention are useful in the inhibition of HIV protease, the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymtomatic, and actual or potential exposure to HIV. For example, the compounds of this invention are useful in treating infection by HIV after suspected past exposure to HIV by e.g., blood transfusion, accidental needle stick, or exposure to patient blood during surgery.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be sold for these purposes.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention, or a pharmaceutically-acceptable salt thereof.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, flourocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Dosage levels of the order of 0.02 to 5.0 or 10.0 grams-per-day are useful in the treatment or prevention of the above-indicated conditions, with oral doses two-to-five times higher. For example, infection by HIV is effectively treated by the administration of from 10 to 50 milligrams of the compound per kilogram of body weight from one to three times per day. It will be understood, however, that the specific dose level and frequency of dosage for any particular patient may be varied and will depend upon a variety of factors including the activity of the specific compound employed, the metabolic stability and length of action of that compound, the age of the patient, body weight, general health, sex, diet, mode and time of administration, rate of excretion, drug combination, the severity of the particular condition, and the host undergoing therapy.

The present invention is also directed to combinations of the HIV protease-inhibitory compounds with one or more agents useful in the treatment of AIDS.

EXAMPLE 1

Preparation of cis-N-tert-butyl-decahydro-(4aS, 8aS)-isoquinoline-3(S)-carboxamide, Compound 5

Step 1: Preparation of cis-N-tert-butoxycarbonyl-3-carboxydecahydro-isoquinoline A suspension of L-3-carboxy-1,2,3,4-tetrahydroisoquinoline, 21.3 g, prepared as described by G. E. Hein, et al., J. Am. Chem. Soc., 84, 4487 (1962), in 650 mL of ethanol and 650 mL of water was shaken with 21.3 g of 5% rhodium on carbon under 15 atm of hydrogen at 50° C. until 3 molar equivalents of hydrogen were consumed (6 h). After cooling the catalyst was filtered off and the solvents removed under reduced pressure. After drying, the residue was recrystallized from ethanol affording 8 g of L-cis-3-carboxydecahydroisoquinoline. To a solution of 5 g of L-cis-3-carboxydecahydrosoquinoline in 75 mL of dioxane and 185 mL of dilute sodium carbonate (pH8) was added 7 g of di-tert-butyldicarbonate. After 2 days stirring at room temperature, the mixture was acidified with 1N HCl until pH is 3 and extracted with three 100 mL portions of ethyl acetate. After concentration and drying there was obtained 4.1 g of a white solid.

Step 2: Preparation of cis-N-tert-butyl-decahydro-(4aS, 8aS)-isoquinoline-3(S)-carboxamide To a stirred solution of cis-N-tert-butoxycarbonyl-3-carboxydecahydro-isoquinoline (the product of Step 1), 4.1 g, in 100 mL of tetrahydrofuran cooled to −20° C. was added 2.8 mL of N-methylmorpholine and 2.42 mL of isobutylchloroformate. After 15 min, 2.4 mL of tert-butylamine was added and the mixture allowed to warm to room temperature and stir overnight. The mixture was diluted with 200 mL of ethyl acetate and 100 mL of 10% citric acid. The organic layer was washed with saturated sodium bicarbonate, dried (MgSO$_4$) and concentrated. The resulting white solid was dissolved in 50 mL of ice cold methylene chloride and 25 mL of trifluoroacetic acid. After warming and stirring for 2 h, the solvents were removed under reduced pressure. The residue was dissolved in 100 mL of methylene chloride, washed with 50 mL of saturated sodium bicarbonate, dried and concentrated. The product, 3.0 g, solidified on standing.

EXAMPLE 2

Preparation of 3(S)-azido-(1,2R)-epoxy-4-phenylbutane, Compound 10

A quantity of CuCN, 2.43 g, was added to a solution of butadiene monooxide, 19 g, in 500 mL anhydrous tetrahydrofuran and the mixture was cooled to −78° C. Phenyl magnesium bromide solution in ether, 32 mmol, was added dropwise to this mixture. The reaction mixture was warmed to 0° C. and was stirred until the reaction became homogeneous. The reaction mixture was cooled to −78° C. and 0.29 mole of phenylmagnesium bromide solution in ether was added dropwise for 30 min. The reaction mixture was allowed to warm to room temperature with stirring then quenched by slow addition of saturated NH$_4$Cl (50 mL) followed by NH$_4$OH (30 mL), saturated NH$_4$Cl (200 mL) and H$_2$O (100 mL). Aqueous layer was extracted with two 200 mL portions of ethyl acetate. Combined organic layers were dried and concentrated. The residue was distilled under vacuum (0.1 torr) at 100° C. to give trans-4-phenyl-2-butene-1-ol (38.9 g, 79% pure).

A mixture of powdered 4A molecular sieves, 3 g, titanium tetraisopropoxide, 1.5 mL, and diethyl D-tartrate, 1.1 mL, in anhydrous methylene chloride (350 mL) was cooled to −20° C. and tert-butylhydroperoxide solution in isooctane, 210 mmol, was added slowly with stirring. After 30 minutes at −20° C. a solution of trans-4-phenyl-2-butene-1-ol, 15.3 g, in anhydrous methylene chloride (50 mL) was added dropwise for 20 min at −20° C. The reaction mixture was aged at −20° C. in a freezer for 20 hours. Water (40 mL) was added to the reaction mixture and after 30 minutes at 0° C., 30% NaOH in brine (6 mL) was added. The resulting mixture was stirred for 1 h at room temperature. The organic phase was separated and the aqueous layer was extracted with two 30 mL portions of methylene chloride. Combined organic layers were dried over Na$_2$SO$_4$, diluted with toluene (300 mL) and concentrated. Chromatography on silica gel with 40% ethyl acetate in hexane gave (2R, 3R)-epoxy-4-phenylbutan-1-ol (10.3 g).

A solution of titanium tetraisopropoxide, 5.6 mL, and azidotrimethylsilane, 5.0 mL, in anhydrous benzene (100 mL) was refluxed for 5 h. To this refluxing mixture was added a solution of (2R, 3R)-epoxy-4-phenylbutan-1-ol, 2.6 g, in anhydrous benzene (10 mL). The reaction mixture was refluxed for 15 min, cooled to room temperature and quenched by addition of 5% H$_2$SO$_4$ (150 mL). After stirring the resulting biphasic mixture for 1 h, the organic layer was separated and the aqueous layer was extracted with two 20 mL portions of ethyl acetate. Combined organic layers were washed with saturated sodium bicarbonate (50 mL), dried over MgSO$_4$ and concentrated. The oily azidodiol product was dissolved in chloroform (30 mL) and 2-acetoxyisobutyryl chloride, 2.5 mL, was added. After stirring for 5 h at room temperature, saturated sodium bicarbonate (50 mL) was added and the resulting biphasic mixture was stirred for 10 min. The aqueous layer was extracted with two 30 mL portions of chloroform. Combined organic layers were dried over Na$_2$SO$_4$ and concentrated. The residue was dissolved in anhydrous tetrahydrofuran (10 mL) and solid NaOMe, 0.614 g, was added. After stirring for 3 h at room temperature, saturated NH$_4$Cl (20 mL) was added and the mixture extracted with two 20 mL portions of ethyl acetate. Combined organic layers were dried over MgSO$_4$ and concentrated. Chromatography on silica gel with 8% ethyl acetate in hexanes gave 3(S)-azido-(1, 2R)-epoxy-4-phenylbutane (1.32 g) as an oil.

EXAMPLE 3

Preparation of cis-N-tert-butyl-decahydro-2 [2(R)-hydroxy-4-phenyl-3(S)-azidobutyl ]-(4aS, 8aS )-isoquinoline-3(S)-carboxamide, Compound 11

A mixture of 6.46 g of cis-N-tert-butyl-decahydro-(4aS, 8aS)-isoquinoline-3(S)-carboxamide (product of Example 1) and 10.3 g of 3(S)-azido-(1,2R)-epoxy-4-phenylbutane (product of Example 2) in 200 mL of isopropanol was heated to 80° C. overnight then concentrated to dryness under reduced pressure. Recrystallization from ethyl acetate-hexanes gave 9.63 g of product of melting point 149°–50° C.

EXAMPLE 4

Preparation of cis-N-tert-butyl-decahydro-2 [2(R)hydroxy-4-phenyl-3(S)-aminobutyl ]-(4aS, 8aS)-isoquinoline-3(S)-carboxamide, Compound 12

A solution of 5.0 g of cis-N-tert-butyl-decahydro-2[2(R)-hydroxy-4-phenyl-3(S)-azidobutyl ](4aS,8aS)-isoquinoline-3(S)-carboxamide (product of Example 3) in 200 mL of tetrahydrofuran and 50 mL of methanol was shaken with 1 g of 10% palladium on carbon catalyst under an atmosphere of hydrogen for 48 h. Removal of the catalyst by filtration and concentration under reduced pressure gave 4.68 g of product as a white solid of melting point 165°–166° C.

EXAMPLE 5

Preparation of 3(S)-tetrahydrofuranyl succinimidyl carbonate, Compound 13

A solution of 20 mL of 12.5% phosgene in toluene and 1.0 g of (S)-(+)-3-hydroxytetrahydrofuran was aged in a stoppered flask for 48 hours. The solvents were removed under reduced pressure and the residue dissolved in 30 mL of anhydrous acetonitrile, then cooled in an ice bath. To this cold solution was added 1.7 g of N-hydroxysuccinimide and 1.9 mL of triethylamine. The mixture was aged for 12 hours at 25° C., then concentrated to dryness. The residue was dissolved in 200 mL of ethyl acetate, washed with 2× 50 mL of water, dried over $MgSO_4$ and concentrated to dryness under reduced pressure. The oily residue was dissolved in 10 mL of ethyl acetate passed through a 300 mL of silica gel, eluting with ethyl acetate. Concentration of the eluate to dryness gave 2 g of product as a white crystalline solid.

EXAMPLE 6

Preparation of cis-N-tert-butyl-decahydro-2 [2(R)hydroxy-4-phenyl-3(S)-[3(S)-tetrahydrofuranyloxycarbonylamino ]-butyl]-(4aS, 8aS )-isoquinoline-3(S)carboxamide, Compound A.

A quantity of 100 mg of the product of Example 4 was reacted with 27 μl $Et_3N$, 5 mL $CH_2Cl_2$ and 50 mg of the product of Example 5 was stirred at 25° C. for 12 hrs., then concentrated to dryness, triturated (hexanes), giving the title compound. mp 80°–82° C.
Calc for $C_{29}H_{45}N_3O_5 \cdot 0.25H_2O$ (520.202)
  %C=66.95, %H=8.81, %N=8.08
Found: %C=67.11, %H=8.92, %N=7.85

EXAMPLE 7

Preparation of 2(S)-butane-1,2,4-triol-1,4-dimesylate 2-THP-ether, Compound 16

(S)-Butane-1,2,4-triol-2-THP ether (Compound 15), 15.0 g, was dissolved in 75 mL of dry methylene chloride and 37 mL of triethylamine and cooled to −10° C. Methanesulfonyl chloride, 10.2 ml, was added dropwise over 10 minutes. After stirring at 24° C. for 12 hours, the solvent was evaporated and the residue was taken up in ethyl acetate and washed with saturated aqueous $NaHCO_3$ (1×150 ml), water (1×150 mL) and brine and dried over anhydrous $Na_2SO_4$. Filtration and concentration under reduced pressure afforded 12 g of the title compound as a brown oil.

EXAMPLE 8

Preparation of 3(S)-hydroxytetrahydrothiophene THP-ether, Compound 17

A solution of 2(S)-butane-1,2,4-triol-1,4-dimesylate 2-THP-ether, 12 g, and lithium sulfide, 8 g, in 250 mL of dry DMF was heated to 70° C. for 12 hours. After cooling to 0° C., ether (400 ml) and water (400 ml) were added and the layers were separated. The aqueous layer was reextracted with ether (1×100 ml) and the combined organic layers were washed with water (1×150 mL) and brine and dried over anhydrous $Na_2SO_4$. Filtration and evaporation of the solvent gave a residue which was taken up in $CH_2Cl_2$ (150 ml) and dried with $Na_2SO_4$. Filtration and concentration under reduced pressure afforded 4.2 g of the title compound as a yellow oil.

EXAMPLE 9

Preparation of 3(S)-hydroxytetrahydrothiophene, Compound 18

A solution of 3(S)-hydroxytetrahydrothiophene THP-ether, 4.2 g, and p-toluenesulfonic acid monohydrate, 0.10 g, in 25 mL of methanol was stirred for 12 hours. Saturated aqueous $NaHCO_3$ (10 ml) was added and stirring was continued for 30 min. Evaporation of the solvents gave a residue which was extacted with ethyl acetate (100 ml) and water (10 ml). The layers were separated and the aqueous layer was reextracted with ethyl acetate (3×20 ml) and the combined organic layers were dried over anhydrous $Na_2SO_4$. Filtration and concentration under reduced pressure gave a residue which was purified by chromatography over silica gel. Elution with 1:1 ethyl acetate/hexanes afforded 2.5 g of the title compound as a clear colorless oil.

EXAMPLE 10

Preparation of 3(S)-tetrahydrothienyl-2-pyridyl carbonate, Compound 19

To a stirred solution of 3(S)-hydroxytetrahydrothiophene, 0.150 g, and di(2-pyridyl) carbonate, 0.470 g in 10 mL of dry methylene chloride was added 0.301 ml of triethylamine. After stirring for 12 hours, the mixture was diluted with methylene chloride and washed with saturated aqueous $NaHCO_3$ (10 ml) and brine and dried over anhydrous $Na_2SO_4$. Filtration and concentration under reduced pressure gave a residue which was purified by chromatography over silica gel. Elution with 1:3 ethyl acetate/hexanes afforded 0.30 g of the title compound as an oil.

EXAMPLE 11

Preparation of cis-N-tert-butyl-decahydro-2 [2(R)-hydroxy-4-phenyl-3(S)-[3(S)-tetrahydrothien-3-yloxycarbonylamino]butyl]-(4aS, 8aS)-isoquinoline-3(S)-carboxamide, Compound 20

A solution of 3(S)-tetrahydrothienyl 2-pyridyl carbonate, 0.30 g, and cis-N-tert-butyl-decahydro-2[2(R)-hydroxy-4-phenyl-3(S)-aminobutyl ]-(4aS, 8aS)-isoquinoline-3(S)-carboxamide (Compound 12), 0.40 g in 30 mL of dry methylene chloride was stirred for 12 hours. The mixture was diluted with methylene chloride and washed with saturated aqueous $NaHCO_3$ (10 ml), brine and dried over anhydrous $Na_2SO_4$. Filtration and concentration under reduced pressure gave a residue which was purified by chromatography over silica gel. Elution with 1:1 ethyl acetate/hexanes afforded 0.350 g of the title compound as a white solid: mp 106°–8° C.
Elemental analysis, calc'd. for
$C_{29}H_{45}N_3O_4S \times 0.35\ H_2O$ (538.06):
C, 64.73; H, 8.56; N, 7.81
Found: C, 64.70; H, 8.31; N, 7.83.

EXAMPLE 12

Preparation of cis-N-tert-butyl-decahydro-2 [2(R)-hydroxy-4-phenyl-3(S)-[3(S)-1, 1-dioxotetrahydrothien-3-yloxycarbonylamino]butyl ]-(4aS, 8aS)-isoquinoline-3(S)-carboxamide, Compound 21

To a stirred solution of 0.350 g of cis-N-tert-butyl-decahydro-2[2(R)-hydroxy-4-phenyl-3(S)[ 3(S)-tetrahydrothien-3-yloxycarbonylamino]butyl]-(4aS,8aS)-isoquinoline-3(S)-carboxamide in 30 mL of acetone and 10 ml of water cooled to 0° C. was added 0.350 mL of a 2.5% solution of osmium tetroxide in 2-methyl-2-propanol. The mixture was stirred to 24° C. for 12 hours and concentrated under reduced pressure. The residue was taken up in ethyl acetate (50 ml) and water (20 ml). The layers were separated and the organic layer was washed with brine and dried over anhydrous $Na_2SO_4$. Filtration and concentration under reduced pressure gave a residue which was purified by chromatography over silica gel. Elution with 5:95 methanol/chloroform afforded 0.325 g of the title compound as a white solid: mp 111°–113° C. Elemental analysis, calc'd. for
$C_{29}H_{45}N_3O_6S \times 0.25\ CHCl_3$ (593.61):
C, 59.18; H, 7.68; N, 7.08
Found: C, 59.25; H, 7.52; N, 7.21

EXAMPLE 13

Preparation of hexahydrofuro[2,3*b*]furan-3*a*-ol

To a stirred solution of 10 g of 2-n-butyl-oxy-3-allyl-tetrahydrofuran-3-ol (prepared as described by M. Jalali-Naini and J. Y. Lallemand, Tetrahedron Letters, pp 497–500, 1986) in 10 mL of methanol and 220 mL of methylene chloride cooled to −78° C. was added a stream of ozone until a blue color persisted. The mixture was purged with nitrogen, warmed to 0° C. and diluted with 100 mL of ethanol. To this mixture was added 5 g of $NaBH_4$. After aging at 25° C. for 6 hours, the solvents were removed under reduced pressure and the residue partitioned between 50 mL of 10% citric acid and 3×100 mL of methylene chloride. The organic extracts were dried over $MgSO_4$ and evaporated to ca. 200 mL. To this stirred solution was added 0.10 g of p-toluenesulfonic acid monohydrate. The mixture was heated at reflux for 24 hours, then concentrated to dryness under reduced pressure. Evaporative distillation of the residue at 0.1 mm (110°–130° C.) gave 2 g of the title compound.

EXAMPLE 14

Preparation of tertiary alcohol urethanes

Step A: Preparation of hexahydrofuro[2,3*b*]furan-3*a*-yl succinimidyl carbonate:

To a stirred solution of 1 g of hexahydrofuro[ 2,3*b*]furan-3*a*-ol in 25 mL of 12.5% phosgene in toluene cooled to −10° C. was added 1 mL of pyridine. The mixture was allowed to warm to 25° C. and stir for 4 hours, then concentrated to dryness under reduced pressure. The oily residue after drying under vacuum (1.3 g) was dissolved in 30 mL of anhydrous acetonitrile, then cooled in an ice bath. To this cold solution was added 1.14 g of N-hydroxysuccinimide and 1.3 mL of triethylamine. The mixture was aged for 48 hours at 25° C., then concentrated to dryness. The residue was dissolved in 200 mL of ethyl acetate, washed with 2×50 mL of water, dried over $MgSO_4$ and concentrated to dryness under reduced pressure. Chromatography of the residue with 20% ethyl acetate in methylene chloride gave 0.49 g of product as a white crystalline solid.

Step B: Preparation of N-(2(R)-hydroxy-1(S)-indanyl)-5(S)-(hexahydrofuro[2,3*b* ]-furanyl-3*a*-oxycarbonylamino)-4(S)-hydroxy-6-phenyl-2(R)-(4-(2-(4-morpholinyl)ethoxy)phenyl) methyl hexanamide:

To a stirred suspension of 100 mg of the product of Example 4 in 15 mL of methylene chloride was added 90 mg of hexahydrofuro[2,3*b*]furan-3*a*-yl succinimidyl carbonate and 0.060 mL of triethyl amine. After stirring for 12 hours, the mixture was diluted with 50 mL of chloroform, washed with 10 mL of sat'd. sodium bicarbonate, and concentrated to dryness. Chromatography using 8% MeOH in $CHCl_3$ gave 80 mg of product as a white crystalline solid.
Calc'd for $C_{41}H_{51}N_3O_9$ C, 67.47 H, 7.07 N, 5.76
Found: C, 67.45 H, 6.90 N, 5.77.

EXAMPLE 15

Preparation of 6(R)-methoxy-3(S)-hydroxy-tetrahydro-2H-pyran and 6(S)-methoxy-3(S)-hydroxytetrahydro-2H-pyran To a stirred suspension of (−)-diisopinocamphenylborane (100 mmol in 40 ml of THF) at 0° C. was added 9.1 ml of 6(SR)-methoxy-2,3-dihydro-2H-pyran. The reaction mixture was stirred at 0° C. for 12 h. After this period, the reaction temperature was raised to 25° C. and 22.4 ml of freshly distilled acetaldehyde was added dropwise for 30 min. The resulting mixture was stirred at 25° C. for 6 h and then excess of acetaldehyde was removed under reduced pressure and to it 80 ml of THF was added. The boronate thus obtained was oxidized with 100 ml of 3N sodium hydroxide and 12.5 ml of 30% hydrogen peroxide. The reaction mixture was stirred at room temperature for 6h and then diluted with 200 ml of ether. The layers were separated and the aqueous layer was extracted with ether (2×100 ml). The combined organic extracts were dried over anhydrous $Na_2SO_4$ and evaporated. The residue was loaded over a silica gel column and eluted first with hexanes to remove a-pinene and then with 25% EtOAc in hexanes to provide 6(R)-methoxy-3(S)-hydroxy-tetrahydro-2H-Pyran (major)

and 6(S)-methoxy-3(S)-hydroxy-tetrahydro- 2H-pyran (minor) as colorless oil.

EXAMPLE 16

Preparation of 1-Benzyloxy-2(S)-hydroxy-4-pentene

Copper(I)cyanide (120 mg, 1.34 mmol) was added to a solution of (R)-(–)-2-(benzyloxymethyl)oxirane (2.4 g, 14.6 mmol) in dry THF (200 ml). This mixture was cooled to −78° C. under argon atmosphere. A solution of vinylmagnesium bromide in THF (26 ml, 1M, 26 mmol) was added slowly to the epoxide solution at −78° C. The reaction mixture was stirred for 5 hours while the reaction temperature was allowed to warm to 0° C. Saturated aqueous $NH_4Cl$ and $NH_4OH$ were added to the reaction mixture till the reaction mixture became clear. Organic layer was separated and the aqueous layer was extracted with EtOAc (3×50 ml). Combined organic layers were dried over $MgSO_4$ and concentrated. The residue was purified by chromatography (EtOAc/Hexane=1:9) to give 1-benzyloxy-2(S)-hydroxy-4-pentent (2.6 g, 13.5 mmol) NMR ($CDCl_3$): 7.35 (bs, 5H), 5.84 (m, 1H), 5.14 (d, J=11, 1H), 5.11 (d, J=9, 1H), 4.57 (s, 2H), 3.90 (m, 1H), 3.53 (dd, J=3.4, 9.5, 1H), 3.39 (dd, J=7.4, 9.5, 1H) 2.29 (t, J=1.23, 2H).

EXAMPLE 17

Preparation of 2(R)-hydroxy-5(R)-iodomethyl tetrahydrofuran

Solid $NaHCO_3$ (3.6 g, 42.9 mmol) was added to a solution of 1-benzyloxy-2-(S)-hydroxy-4-pentene (1.1 g, 5.7 mmol) in dry $CH_3CN$ (25 ml) and the resulting mixture was cooled to 0° C. To this mixture was added a solution of iodine (2.9 g) in dry acetonitrile. Then the reaction mixture was stirred for 3 hours at 0° C. Saturated $NaHCO_3$ (50 ml) was added to the reaction mixture. Solid $NaHCO_3$ was added to the biphasic mixture until the iodine color disappeared. Organic layer was separated and the aqueous layer was extracted with EtOAc (3×50 ml). Combined organic layers were dried over $MgSO_4$ and was concentrated. The reside was purified by chromatography (EtOAc/hexane 1:1) to give the 20(S)-hydroxy-5(R)-iodomethyltetrahydrofuran (232.3 mg), a mixture of isomers (171.5 mg) and 2-(R)-hydroxy-5-(R)-iodomethyltetrahydrofuran (663.1 mg). NMR ($CDCl_3$):
2-(S)-hydroxy-5-(R)-iodomethyltetrahydrofuran: 4.52 (m, 1H), 4.03 (m, 1H), 3.98 (dd, J=10.8, 1.5, 1H), 3.81 (dd, J=4.1, 10.8 1H), 3.44 (dd, J=10, 6.5, 1H), 3.36 (dd, J=10, 5.3, 1H), 2.36 (m, 1H), 1.84 (m, 1H).
2-(R)-hydroxy-5-(R)-iodomethyltetrahydrofuran: 4.58 (bs, 1H), 4.22 (m, 1H), 4.09 (dd, J=9.9, 4.1, 1H), 3.30 (d, J=5.6, 2H), 2.17 (dd, J=13.3, 5.8, 1H), 1.81 (m, 1H).

EXAMPLE 18

Preparation of 2(S,R)-(methylethyl)-3(S,R)-hydroxytetrahydrothiophene

Ethyl 3-mercaptopropionate (22.46 g) was dissolved in absolute ethanol (60 mL) and the solution was cooled to −20° C. To it was added sodium ethoxide solution in ethanol (62.5 mL of 21%). A solution of ethyl 2-bromoisovalerate (35 g) in absolute ethanol (60 mL) was added slowly. The reaction mixture was stirred for 2 hours while the reaction temperature was allowed to warm to room temperature. Saturated $NH_4Cl$ (150 mL) was added to the reaction mixture and organic layer was separated. The aqueous layer was extracted with ethyl acetate (100 mL×3). The combined organic layers were dried over $Na_2SO_4$ and concentrated. Sodium (0.88 g) was dissolved in absolute ethanol (40 mL) at 0° C. and the solution was concentrated. The residue was dissolved in toluene and the product from the previous reaction (7.78 g) was added. The reaction mixture was treated to reflux for 2 hours. The reaction mixture was cooled to room temprature and 1N HCl was added to the reaction mixture until the pH became acidic. The crude product was extracted with EtOAc (50 mL×3) and the combined organic layers were washed with brine, were dried over $Na_2SO_4$ and concentrated. The residue was heated with 10% $H_2SO_4$ (40 mL) at 100° C. overnight. The crude product was extracted with ethyl acetate (50 mL× 3). The combined organic layers were dried over $Na_2SO_4$ and concentrated. The residue (2(S,R)-(methylethyl)-tetrahydrothiophen-3-one) was dissolved in methylene chloride (60 mL) and the solution was cooled to 0° C. Diisobutylaluminumhydride (25 mL, 1M) in methylene chloride was added dropwise. The reaction mixture was stirred for one hour at 0° C. The reaction was quenched by the dropwise addition of water until no gas evolved. 1N HCl (50 mL) was added and the crude product was extracted with methylene chloride (50 mL× 3). Combined organic layers were washed with saturated $NaHC_3$, brine and dried over $Na_2SO_4$. Concentration and purification by column chromatography, eluting with 20% ethyl acetate in hexane gave an oil (1.72 g):
$^1$NMR ($CDCl_3$): 4.36 (br, s, 1H), 3.1–2.85 (m, 3H), 2.23 (dd, J=6.8 Hz, 13.3 Hz, 1H), 1.95–1.77 (m, 3H), 1.07 (d, J=6.5 Hz, 3H), 1.02 (d, J=6.7 Hz, 3H).

EXAMPLE 19

Preparation of 3(R,S)-[2(R,S)-methylethyl]tetrahydrothienyl-2-pyridyl carbonate

To a stirred solution of 2(R,S)-methylethyl-3(R,S)-hydroxytetrahydrothiophene, 0.150 g and di (2 pyridyl) carbonate, 0.250 g in 3 mL of dry methylene chloride was added 0.185 mL of triethylamine. After stirring for 12 hours, the mixture was diluted with methylene chloride and washed with saturated aqueous $NaHCO_3$ and brine and dried over anhydrous $Na_2SO_4$. Filtration and concentration under reduced pressure gave the title compound as an oil.

EXAMPLE 20

Preparation of N-tert-butyl-decahydro-2[2(R)-hydroxy- 4-phenyl-3(S)-[1,1-dioxo-2(R)-methylethyl-3(R)-tetrahydrothienyloxycarbonylamino] butyl]-(4aS, 8aS) isoquinoline-3(S)-carboxamide, Compound C To a stirred solution of 2(R,S)-methylethyl-2(R,S)-tetrahydrothienyl 2-pyridyl carbonate, 0.203 g, and N-tert-butyl-decahydro-2[2(R)-hydroxy-4-phenyl-3(S)-aminobutyl]-(4aS,8aS)-isoquinoline-3 (S)-carboxamide, 0.204 g in 5 mL of dry methylene chloride was added 0.093 mL of triethylamine. After stirring for 12 hours the mixture was diluted with methylene chloride and washed with saturated aqueous $NaHCO_3$, brine and dried over anhydrous $Na_2SO_4$.

Filtration and concentration under reduced pressure gave a residue which was purified by chromatography over silica gel. Elution with 1:4 ethyl acetate/hexane and by 1:1 ethyl acetate/hexane afforded 0.217 g of N-tert-butyl-decahydro-2[2(R)-hydroxy- 4-phenyl-3(R,S)-[2(R,S)-methylethyl-3(R, S)-tetrahydrothienyloxycarbonylamino] butyl]-(4aS,8aS)- isoquinoline-3(S)-carboxamide. To a stirred solution of this compound and 0.250 g of N-methylmorpholine oxide in 10 mL of acetone and 2 mL of water was added 0.1 mL of a 2.5% solution of osmium tetroxide in 2-methyl-2propanol. The mixture was stirred for 12 hours and 1.3 mL of saturated aqueous NaHSO₃ was added to it. The mixture was extracted with methylene chloride (20 mL). The organic solution was washed with saturated aqueous NaHSO₃, brine and dried over $Na_2SO_4$.

Filtration and concentration under reduced pressure gave a residue which was purified by chromatography over silica gel. Elution with 1:1 ethyl acetate/hexane and by 3:1 ethyl acetate/hexane afforded 0.035 g of N-tert-butyl-decahydro-2[2(R)-hydroxy-4-phenyl-3(S)-[1,1-dioxo-2(R)-methyl-ethyl-3 (R)-tetrahydrothienyloxycarbonylamino]butyl]-(4aS,8aS)-isoquinoline-3(S)-carboxamide as a white amorphous solid:

m.p. 115°–117° C.;
¹NMR (CDCl₃): 7.29-7.18 5H), 5.80 (bs, 1H), 5.25 (bs, 1H), 3.99-3.82 (m, 3H), 3.20-2.85 (m, 5H), 2.66 (m, 2H), 2.31 (m, 2H), 1.36 (s, 9H), 1.17 (d, J=6.5 Hz, 3H) , 0.94 (d, J=6.5 Hz, 3H).

Elemetnal analysis, calc'd for $C_{33}H_{51}N_3O_6S \times 0.60$ $CH_2Cl_2 \times 0.05\ H_2O$ (657.70):
C, 59.54; H, 8.02; N, 6.39
Found: C, 59.53; H, 7,5 4; N, 6.23

Further elution with 5:95 methanol/chloroform gave N-tert-butyl-decahydro-2[2(R)-hydroxy-4-phenyl- 3(S)-[1, 1-dioxo-2(S)-methylethyl-3(S)-tetrahydrothienyloxycarbonylamino] butyl]-(4aS, 8aS)-isoquinoline-3(S)-carboxamide: m.p. 110°–112° C.

Elemetnal analysis, calc'd for $C_{33}H_{51}N_3O_6S \times 0.75\ H_2O$ (654.49):
C, 62.06; H, 8.54; N, 6.78
Found: C, 62.02; H, 8.33; N, 6.40

EXAMPLE

Assay for Inhibition of Microbial Expressed Viral Protease

Inhibition studies of the reaction of the protease expressed in Escherichia coli with a peptide substrate [Val-Ser-Gln-Asn-(betanapthyl)Ala-Pro-Ile-Val, 0.5 mg/mL at the time the reaction is initiated] were in 50 mM Na acetate, pH 5.5, at 30° C. for 1 hour. Various concentrations of inhibitor in 1.0 ul DMSO were added to 25 ul of the peptide solution in water. The reaction is initiated by the addition of 15 ul of 0.33 nM protease (0.11 ng) in a solution of 0.133 M Na acetate pH 5.5 and 0.26% bovine serum albumin. The reaction was quenched with 160 ul of 5% phosphoric acid. Products of the reaction were separated by HPLC (VYDAC wide pore 5 cm C-18reverse phase, acetonitrile gradient, 0.1% phosphoric acid). The extent of inhibition of the reaction was determined from the peak heights of the products. HPLC of the products, independently synthesized, proved quantitation standards and confirmation of the product composition. Compounds A , B and C showed $IC_{50}$ values of about 260 nM, 59 nM and 4 nM respectively.

While the foregoing specification teaches the principles of the present invention, with examples provided for the purpose of illustration, it will be understood that the practice of the invention encompasses all of the usual variations, adaptations, or modifications, as come within the scope of the following claims and its equivalents.

What is claimed is:
1. A compound

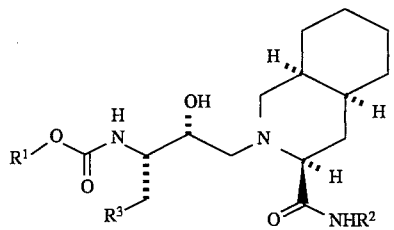

wherein:
$R^1$ is a) 5- to 7- membered carbocylic ring which is either saturated, partially saturated or unsaturated, the carbocylic ring being unsubstituted or substituted with one or more of $C_{1-4}$ alkyl, $C_{2-4}$ alkenyl, $C_{1-3}$ alkoxy, halo-$C_{1-3}$ alkyl, aryl-$C_{1-3}$ alkyl, or $C_{3-5}$ cycloalkyl; or b) 5- to 7-membered heterocyle having one heteroatom selected from O or S, any of which heterocycle is unsubstituted or substituted with one or more of $C_{1-4}$ alkyl, $C_{2-4}$ alkenyl, oxo, $C_{3-5}$ cycloalkyl, or $C_{1-3}$ alkoxy;

$R^2$ is a) $C_{1-5}$ alkyl, unsubstituted or substituted with one or more of —OH or $C_{1-3}$ alkoxy; or 5- to 7-membered carbocyclic ring which is either saturated, partially saturated or unsaturated, the carbocyclic ring being unsubstituted or substituted with one or more of $C_{1-4}$ alkyl, $C_{2-4}$ alkenyl, $C_{1-3}$ alkoxy, or hydroxy;

$R^3$ is a) Phenyl unsubstituted or substituted with one or more of —OH or $C_{1-3}$ alkoxy; or $C_{5-7}$ cycloalkyl unsubstituted or substituted with one or more of —OH or $C_{1-3}$ alkoxy,
or pharmaceutically acceptable salt or hydrate thereof.

2. A compound according to claim 1, wherein:
$R^1$ is a 5- to 7-membered heterocycle having one heteroatom selected from O or S, any of which heterocycle is unsubstituted or substituted with one or more of $C_{1-4}$ alkyl, $C_{2-4}$ alkenyl, oxo or $C_{1-3}$ alkoxy;

$R^2$ is $C_{1-5}$ alkyl, unsubstituted or substituted with one or more of —OH.

$R^3$ is phenyl unsubstituted or substituted with —OH or $C_{1-3}$ alkoxy.

3. A compound according to claim 2 wherein:
$R^1$ is 1,1-dioxo-tetrahydrothienyl or tetrahydrofuranyl, unsubstituted or substituted with $C_{1-4}$ alkyl, $C_{2-4}$ alkenyl or $C_{1-3}$ alkoxy;

$R^2$ is t-butyl or 2-methylpropyl;

$R^3$ is phenyl.

4. A compound according to claim 3, wherein:
$R^1$ is tetrahydrofuran-3-yl or 1,1-dioxo-tetrahydrothien-3-yl, unsubstituted or substituted with methyl, ethyl, n-propyl, i-propyl, methoxy, ethoxy, or propenyl.

5. A compound according to claim 1, wherein:
$R^1$ is a 5- to 7-membered heterocycle having one S heteroatom, said heterocycle unsubstituted or substituted with one or more of $C_{1-4}$ alkyl, oxo or $C_{3-5}$ cycloalkyl $R^2$ is $C_{1-5}$ alkyl;

$R^3$ is phenyl.

6. A compound according to claim 5, wherein:
$R^1$ is 1,1-dioxotetrahydrothien-3-yl, unsubstituted or substituted with $C_{1-4}$ alkyl, or $C_{3-5}$ cycloalkyl $R^2$ is $C_{1-5}$ alkyl;

$R^3$ is phenyl.

7. The compound,

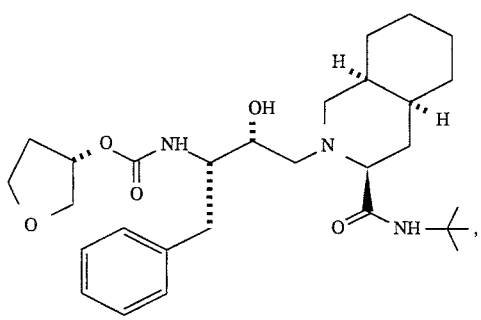

named:
cis-N-tert-butyl-decahydro-2[2(R)-hydroxy-4-phenyl-3(S)-[3(S)-tetrahydrofuranyloxycarbonylamino]-butyl]-(4aS,8aS)-isoquinoline-3(S)-carboxamide hydrate, or pharmaceutically acceptable salt thereof.

8. The compound,

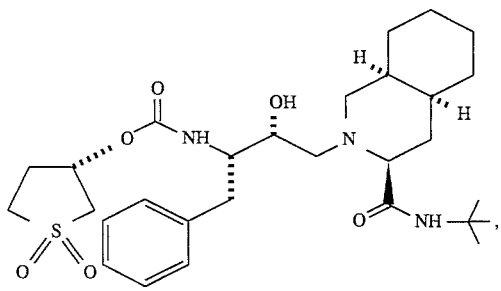

named:
Cis-N-tert-butyl-decahydro-2[2(R)-hydroxy-4-phenyl-3(S)-[3(S)-1,1-dioxotetrahydrothien-3-yloxycarbonylamino]-butyl]-(4aS,8aS)-isoquinoline-3(S)-carboxamide hydrate, or pharmaceutically acceptable salt thereof.

9. The compound,

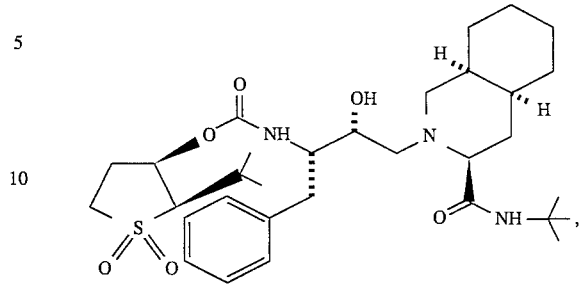

N-tert-butyl-decahydro-2[2-(R)-hydroxy-4-phenyl-3(S)-[1,1-dioxo-2(R)-methylethyl-3(R)-tetrahydrothienyloxycarbonylamino]butyl]-(4aS,8aS)-isoquinoline-3(S)-carboxamide, or pharmaceutically acceptable salt thereof.

10. Pharmaceutical composition, for use in the treatment of AIDS, in the treatment of infection of HIV, or in the inhibition of HIV protease, comprising an effective amount of a compound as in any of claims 1–9, and a pharmaceutically acceptable carrier.

11. A method of treating AIDS, comprising administering an effective amount of a compound as in any claims 1–9.

12. A method of treating infection by HIV, comprising administering an effective amount of a compound as in any of claims 1–9.

13. A method of inhibiting HIV protease, comprising administering an effective amount of a compound as in any of claims 1–9.

* * * * *